(12) United States Patent
Gulabani et al.

(10) Patent No.: US 10,487,406 B2
(45) Date of Patent: Nov. 26, 2019

(54) BIS-IMIDAZOLINE COMPOUNDS AS CORROSION INHIBITORS AND PREPARATION THEREOF

(71) Applicant: Dow Global Technologies LLC, Midland, MI (US)

(72) Inventors: Ritesh Gulabani, Vadodara (IN); Stephen W. King, League City, TX (US); Deepak Dicholkar, Vitawa (IN); Sung-Yu Ku, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 277 days.

(21) Appl. No.: 15/107,782

(22) PCT Filed: Dec. 12, 2014

(86) PCT No.: PCT/US2014/069930
§ 371 (c)(1),
(2) Date: Jun. 23, 2016

(87) PCT Pub. No.: WO2015/100031
PCT Pub. Date: Jul. 2, 2015

(65) Prior Publication Data
US 2016/0319442 A1 Nov. 3, 2016

(30) Foreign Application Priority Data

Dec. 27, 2013 (IN) .......................... 6133/CHE/2013

(51) Int. Cl.
| C23F 11/14 | (2006.01) |
|---|---|
| C07D 233/06 | (2006.01) |
| C07D 233/10 | (2006.01) |
| C23F 11/04 | (2006.01) |
| C09D 5/12 | (2006.01) |
| C09D 5/08 | (2006.01) |

(52) U.S. Cl.
CPC .......... *C23F 11/149* (2013.01); *C07D 233/06* (2013.01)

(58) Field of Classification Search
CPC ........ C23F 11/14; C23F 11/04; C07D 233/06; C07D 233/10; C09D 5/086; C09D 7/125
See application file for complete search history.

(56) References Cited

U.S. PATENT DOCUMENTS

| 2,918,474 A | * | 12/1959 | Hughes ............ C06B 45/18 |
|---|---|---|---|
| | | | 252/392 |
| 3,578,589 A | | 5/1971 | Hwa et al. |
| 4,482,724 A | | 11/1984 | Ritschel et al. |
| 4,501,667 A | | 2/1985 | Cook |
| 4,566,973 A | | 1/1986 | Masler, III et al. |
| 4,614,600 A | | 9/1986 | Schilling et al. |
| 4,675,158 A | | 6/1987 | Klindera |
| 4,713,184 A | | 12/1987 | Zaid |
| 4,744,950 A | | 5/1988 | Hollander |
| 5,038,861 A | | 8/1991 | Shuler |
| 5,308,498 A | | 5/1994 | Fong et al. |
| 5,611,992 A | | 3/1997 | Naraghi et al. |
| 5,772,919 A | | 6/1998 | Reichgott et al. |
| 6,464,901 B1 | | 10/2002 | Cheng |
| 6,475,914 B2 | | 11/2002 | Han |

FOREIGN PATENT DOCUMENTS

| CA | 2 394 440 A1 | 7/2002 |
|---|---|---|
| CA | 2 398 423 A1 | 8/2002 |
| CN | 1422984 A | 6/2003 |
| CN | 1584121 A | 2/2005 |
| CN | 101565608 A | 10/2009 |
| CN | 101613622 A | 12/2009 |
| CN | 101962366 A | 2/2011 |
| DE | 3135235 A1 | 3/1983 |
| DE | 40 39 271 A1 | 6/1992 |
| EP | 0 490 161 A2 | 6/1992 |
| JP | H6268356 A | 9/1994 |
| JP | 9241636 A | 9/1997 |
| JP | 2000096272 A | 4/2000 |
| MX | PA03011620 A | 6/2005 |
| MX | PA03011659 A | 6/2005 |
| RU | 2357007 C2 | 1/2009 |
| SU | 1526283 A1 | 10/1992 |
| WO | 1996/031749 A1 | 10/1996 |
| WO | 0049204 A1 | 8/2000 |
| WO | 2008/031781 A2 | 3/2006 |
| WO | 2009088702 A1 | 7/2009 |

OTHER PUBLICATIONS

Antonijevic et al., "Copper Corrosion Inhibitors. A Review", International Journal of Electrochemical Science, 3 (Jan. 1, 2008) 1-28.
Wu et al., "Chiral NCN Pincer Pt(II) Complexes with 1,3-Bis(2'-imidazolinyl)benzene: Synthesis via Direct Metalation Characterization, and Catalytic Activity in the Friedel—Crafts Alkylation Reaction", Organometallics 2009, 28, 3369-3380 (received Oct. 19, 2008).
Zhao, et al. (2012) "The synergistic inhibition effect of oleic based imidazoline and sodium benzoate on mild steel corrosion in a CO2 saturated brine solution", Electrochimica Acta 69:247-255.
Demadis, et al. (2007) "Degradation of Phosphonate-Based Scale Inhibitor Additives in the Presence of Oxidizing Biocides: "Collateral Damages" in Industrial Water Systems", Separation Science and Technology, 42:1639-1649.

(Continued)

*Primary Examiner* — Robert D Harlan
(74) *Attorney, Agent, or Firm* — Kagan Binder, PLLC (57) ABSTRACT

The disclosure provides compositions and methods for inhibiting corrosion of a copper surface using a bis-imidazoline compound having an aromatic group, such as an aryl bis-imidazoline. The bis-imidazoline corrosion inhibitor can provide one or more advantage in use such as synergistic performance in aqueous and acidic media at low active dosages, resistance to decomposition or degradation in the presence of harsh reagents, ease of dispersion in an aqueous system, and improved thermal stability over conventional triazole based inhibitors. The disclosure also provides methods for the synthesis of bis-imidazoline compounds.

19 Claims, 2 Drawing Sheets

(56) References Cited

OTHER PUBLICATIONS

Shin, et al. (1996) "A New Synthetic Route to Poly(benzimidazole) and the Related Model Reactions to Imidazoline and Benzimidazole", Bull. Korean Chem. Soc., 17(1):29-33.
Braddok, et al. (2010) "The reaction of aromatic dialdehydes with enantiopure 1,2-diamines: an expeditious route to enantiopure tricyclic amidines", Tetrahedron: Asymmetry, 21:2911-2919.

* cited by examiner

BIS-IMIDAZOLINE COMPOUNDS AS CORROSION INHIBITORS AND PREPARATION THEREOF

CROSS-REFERENCE TO RELATED APPLICATIONS

This application claims priority to International Application No. PCT/US2014/069930, filed Dec. 12, 2014, which in turn claims priority to Indian Patent Application No. 6133/CHE/2013, filed Dec. 27, 2013, wherein the disclosures of these applications are incorporated herein by reference in their respective entireties for all purposes.

BACKGROUND

Water-based compositions are used in many industrial processes to help cool or clean metal components of industrial or residential equipment, shipping containers, plumbing and fixtures, buildings, land-based transportation systems, marine-based systems or habitats, or aeronautical systems or habitats. Water also may be a part of a solvent or other constituent of compositions that are being transported, processed, or otherwise handled by such items. Many types of metal components in such systems may contact water-based compositions including heat exchangers, pipes, tanks, valves, water pumps, pump impellers, propellers, and turbine plates, housings, work surfaces, fasteners, supports, computer components, hardware, etc. Metals include pure metals, alloys, intermetallic compositions, or other metal-containing compositions that are susceptible to corrosion.

Water-based compositions, for example, those that are used as heat exchange media, may damage metal components by causing erosion or corrosion of the metal. Corrosion generally is a destructive attack on metal involving oxidation or other chemical attack. For example, the presence of certain ions and biocides can increase oxidation and thereby accelerate the erosion or corrosion of items at risk.

Corroded metal components can have reduced functionality, causing inefficiencies or inoperability of the industrial process. Corroded components may need to be discarded, repaired or replaced. In addition, corrosion products accumulate and may decrease the rate of heat transfer between the corroded material and the water or other fluid media. Therefore, corrosion may reduce the efficiency of the system operation where efficient cooling is a factor. Corrosion of metallic components in industrial plants can cause system failures and even plant shutdowns.

The corrosion can also lead to the undesirable release of copper in the water-based composition. Dealing with the used water-based composition can also be problematic, especially for large volume industrial systems.

Triazole-based compounds have been used to inhibit corrosion of copper surfaces in industrial processes. Triazole-based corrosion inhibitors can form a film on a copper surface to protect against the damaging components of the aqueous composition. Triazole-based compounds such as benzotriazole and tolyltriazole are known copper corrosion inhibitors (see, for example, U.S. Pat. No. 4,675,158). U.S. Pat. No. 4,744,950 discloses the use of lower (e.g., $C_3$-$C_6$ linear alkyl, especially n-butyl) alkylbenzotriazoles as corrosion inhibitors in an aqueous system.

However, the preparation and use of triazole compounds can be problematic. For example, triazole performance is adversely affected in the presence of halogenated biocidal additives (e.g. hypochlorites). Also, tolyltriazole which is commonly used as a corrosion inhibitor for copper and copper alloys is manufactured from intermediates of the toluene nitration process for the preparation of toluene diamines which are used for the synthesis of toluene diisocyanate (TDI). These intermediates can be undesirable to work with and could potentially be non sustainable.

SUMMARY

The disclosure of the invention in some aspects is directed to aqueous compositions and methods for inhibiting corrosion of a copper-containing component using a bis-imidazoline corrosion inhibitor. For example, the composition can be used in an industrial water treatment composition for cooling or treating where the composition comes into contact with a system article having a copper surface. In other aspects, the disclosure is directed to methods of preparing bis-imidazoline compounds. The disclosure also provides novel bis-imidazoline compounds.

Embodiments of the invention include methods for inhibiting corrosion of an article comprising a metal surface that includes copper, in an aqueous system. The method includes a step of contacting the article with an aqueous composition comprising a compound of Formula I:

In Formula I, $R^1$ is a partially or fully unsaturated, single or fused cyclic C3-C14 hydrocarbylene group having aromaticity, optionally substituted and optionally having one or more heteroatoms. In Formula I, $R^2$, $R^3$, $R^4$, $R^5$, $R^6$, and $R^7$ are independently selected from H and $R^8$, wherein $R^8$ is a hydrocarbyl group optionally including one or more N, O, or S heteroatoms.

Embodiments of the invention also include aqueous compositions capable of inhibiting corrosion of an article comprising a copper surface. The composition includes (a) a corrosion inhibiting amount of a compound of Formula I, and (b) one or more component(s) selected from the group consisting of a dispersant, a surfactant, a pH adjuster, a biocide, a scale inhibitor, and a defoamer.

Embodiments of the invention also include methods for preparing an aryl bis-imidazoline compound. The method includes a step of reacting an aryl acid or aryl acid halide with an alkylene diamine to provide an aryl-bis-imidazoline compound. In exemplary methods the aryl acid or aryl acid halide is a compound of Formula XI:

wherein $R^{13}$ is H, a halogen, or a linear, branched or cyclic hydrocarbyl group, optionally including one or more heteroatoms, wherein X is a halogen or —OH, and wherein n is 0, or an integer in the range of 1-4, and y is 2, and the alkylene diamine is a compound of Formula XII, wherein $R^{14}$ and $R^{15}$ are independently selected from H and hydrocarbyl groups optionally including one or more N, O, or S heteroatoms, and m is 2.

The bis-imidazoline based corrosion inhibitors of the current disclosure have been found to provide improved and synergistic corrosion inhibition performance, especially for non-ferrous metals (e.g. copper) in aqueous and acidic media at low active dosages. Improved and synergistic corrosion inhibition can also be observed in combination with other components such as dispersants and surfactants.

It is thought that a mechanism of corrosion inhibition is provided at least in part by formation of a stable film (e.g., mono-layer adsorption of the bis-imidazoline based corrosion inhibitors; "film persistence"). The presence of electron-donating hetero atoms/functionality, aromaticity with pi electrons, and planarity of structure of the bis-imidazoline compound is believed to enhance its binding or adsorption to the surface (passivation). The bis-imidazoline corrosion inhibitor also showed ease of dispersion in an aqueous system leading to efficient performance even at low active dosages. Improved film persistence and passivation can provide economic and ecologic advantages in that lower doses of the compound are needed to provide an anti-corrosive effect.

Further, the bis-imidazoline corrosion inhibitor demonstrates improved thermal stability over conventional triazole based inhibitors. Experimental studies revealed that at high temperatures which caused complete degradation of a triazole inhibitor, only low levels of degradation of the bis-imidazoline corrosion inhibitor were observed. Therefore, the bis-imidazoline corrosion inhibitors can promote a more efficient and sustainable performance under stringent field conditions.

DETAILED DESCRIPTION

Reference will now be made in detail to representative embodiments of the invention. While the invention will be described in conjunction with the enumerated embodiments, it will be understood that they are not intended to limit the invention to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods, materials, and compositions described.

Unless defined otherwise herein, technical and scientific terms used herein have the same meaning as commonly understood by one of ordinary skill in the art to which this invention belongs. Although any methods, devices, and materials similar or equivalent to those described herein can be used in the practice or testing of the invention, exemplary methods, devices and materials are now described.

Bis-imidazoline compounds of the current disclosure include those of Formula I:

In Formula I, as well as other bis-imidazoline formulas including $R^1$ herein, $R^1$ is a partially or fully unsaturated, single or fused cyclic C3-C14 hydrocarbylene group (a divalent hydrocarbon-containing group) having aromaticity, optionally substituted and optionally having one or more heteroatoms.

In some aspects, $R^1$ includes an aryl group, optionally ring substituted, which can provide the aromaticity (i.e., aromatic chemical feature). An "aryl group" refers to a chemical group derived from an aromatic ring. For example, $R^1$ can include an aryl group represented by a benzene ring, which optionally can be ring fused to another aryl group, or to a partially saturated or unsaturated ring structure. Exemplary aryl groups include phenylene, naphthylene, anthracylene, phenanthrylene, biphenylene and indylene, optionally ring substituted. In more specific embodiments, R' is phenylene, optionally ring substituted.

Carbon atoms on the same aromatic ring of R' can be bonded to the imidazol-based rings (a) and (b), e.g., in para, meta, or othro configurations. The location of the imidazol-based rings (a) and (b) can optionally be described with regards to chemical numbering around the aromatic ring (i.e., two of positions 1, 2, 3, 4, 5, and 6). Accordingly, the disclosure provides compounds of Formula II:

In other embodiments, R' includes two or more aryl groups (e.g., naphthylene, anthracylene) and carbon atoms on the different aromatic rings of $R^1$ can be individually bonded to the imidazol-based rings (a) and (b), such as reflected by Formula III:

In Formula I, or any other bis-imidazoline formula herein, $R^2$, $R^3$, $R^4$, $R^5$, $R^6$, and $R^7$ are independently selected from H and $R^8$, wherein $R^8$ is a hydrocarbyl group optionally including one or more N, O, or S. Hydrocarbyl groups as referred to herein are substituted or unsubstituted, linear, branched, or cyclic hydrocarbyl groups, such as alkyl, aryl, aralkyl, or the like. Exemplary hydrocarbyl groups include linear or branched C1-C12 groups, optionally including one or more N, O, or S heteroatoms, such as methyl, ethyl, n-propyl, isopropyl, isobutyl, t-butyl, sec-butyl, ethylamine, propylamine, ethoxy, propoxy, etc.

In some embodiments, the disclosure provides a compound of formula IV:

In Formula IV, $R^9$ is H, a halogen, or a linear, branched or cyclic hydrocarbyl group, optionally including one or more heteroatoms, and wherein n is 0, or an integer in the range of 1-4. In some embodiments $R^9$ of any of the formulas herein is selected from the group consisting of —H, methyl, and ethyl.

Exemplary compounds of Formula IV include 1,4-bis(4,5-dihydro-1H-imidazol-2-yl)benzene (also referred to as "phenyl bis-imidazoline" shown herein); 1,3-bis(4,5-dihydro-1H-imidazol-2-yl)benzene and 1,2-bis(4,5-dihydro-1H-imidazol-2-yl)benzene.

Another compound of Formula I includes 1,4-bis(4,5-dihydro-1H-imidazol-2-yl)naphthalene:

In other embodiments, where one or both of $R^2$ and $R^3$ of Formula I are $\sim R^{10}{}_x CH_2CH_2NH_2$, wherein, $R^{10}$ is $\sim(CH_2CH_2NH)\sim$, x is 0 or an integer in the range of 1-3, which provides a compound of Formula V:

Included in Formula V are compounds of Formula VI:

Exemplary compounds of Formula VI include: 2,2'-(2,2'-(1,4-phenylene)bis(4,5-dihydro-1H-imidazole-2,1-diyl))diethanamine (shown below); and N1,N1'-((2,2'-(1,4-phenylene)bis(4,5-dihydro-1H-imidazole-2,1-diyl))bis(ethane-2,1-diyl))bis(ethane-1,2-diamine).

In other embodiments, one or both of $R^2$ and $R^3$ are $\sim R^{10}{}_x[CH(R^{11})CH(R^{12})O]_yH$ wherein $R^{10}$ is $\sim(CH_2CH_2NH)\sim$, x is 0 or an integer in the range of 1-3, $R^{11}$ and $R^{12}$ are independently selected from the group consisting of hydrogen, methyl, and/or ethyl; y is 0 (a covalent bond) or an integer in the range of 1-5, such as reflected by Formulas VII and VIII, respectively, as follows:

Included in Formulas VII and VIII, are compounds of Formulas IX and X, respectively, as follows:

wherein $R^{10}$ is ~(CH$_2$CH$_2$NH)~, x is 0 or an integer in the range of 1-3, $R^{11}$ and $R^{12}$ are independently selected from the group consisting of hydrogen methyl and/or ethyl; y is 0 (a covalent bond) or an integer in the range of 1-5.

Exemplary compounds of Formulas IX and X include: 2,2'-(2,2'-(1,4-phenylene)bis(4,5-dihydro-1H-imidazole-2,1-diyl))diethanol; 1,1'-(2,2'-(1,4-phenylene)bis(4,5-dihydro-1H-imidazole-2,1-diyl))bis(propan-2-ol); 1,1'-(2,2'-(1,4-phenylene)bis(4,5-dihydro-1H-imidazole-2,1-diyl))bis(butan-2-ol); 2,2'-(((2,2'-(1,4-phenylene)bis(4,5-dihydro-1H-imidazole-2,1-diyl))bis(ethane-2,1-diyl))bis(oxy))diethanol; 1,1'-(2,2'-(1,4-phenylene)bis(4,5-dihydro-1H-imidazole-2,1-diyl))bis(propan-2-ol); 2,2'-(2,2'-(1,4-phenylene)bis(1H-benzo[d]imidazole-2,1-diyl))diethanol; and 1,1'-(2,2'-(1,4-phenylene)bis(1H-benzo[d]imidazole-2,1-diyl))bis(propan-2-ol).

The disclosure also provides methods for preparing, aryl-bis-imidazoline compounds. In one mode of synthesis, the method includes a step of reacting an aryl diacid or aryl diacid halide with an alkylene diamine to provide a bis aryl-imidazoline compound. In exemplary modes of synthesis the aryl diacid or aryl diacid halide is a compound of Formula XI:

$R^{13}$ is H, a halogen, or a linear, branched or cyclic hydrocarbyl group, optionally including one or more heteroatoms, wherein X is a halogen or —OH, and wherein n is 0, or an integer in the range of 1-4, and y is 2. The alkylene diamine is a compound of Formula XII:

where $R^{14}$ and $R^{15}$ are independently selected from H and hydrocarbyl groups optionally including one or more N, O, or S heteroatoms, and m is 2.

In the reaction, the alkylene diamine can be used in an amount (molar) of about two times or greater the amount aryl diacid or aryl diacid halide, such as about 2 to about 6, or about 4 times molar excess. The reaction can be carried out by increasing the temperature during the course of the reaction. For example, the reaction temperatures are in the range of about 100° C. to about 325° C., which are increased from a temperature in the low end of the range to a temperature in the upper end of the range. In exemplary embodiments, the reaction is heated at about 120° C. and held for about 2 hours, then increased to about 200° C. and held for about 2 hours, and then increased to about 300° C. and held for about 3 hours.

In some modes of practice, aryl bis-imidazoline compounds can be prepared by reacting an aryl diacid, or an aryl diacid halide, such as terephthaloyl dichloride, with an alkylene diamine, such as ethylenediamine, using methods as described herein.

The reaction can be carried out by increasing the temperature during the course of the reaction. For example, the reaction can initially begin at room temperature and then be raised throughout the course of the reaction, such as to a temperature in the range of about 100° C. to about 120° C. and holding for a period of three hours, followed by increasing to a temperature in the range of about 280° C. to about 300° C., under reduced pressure.

In some modes of practice, some bis-imidazoline compounds for use in aqueous compositions of the invention can be prepared using art-known techniques. For example, JP 42001548 describes reaction of an aliphatic 1,2-diamine with a nitrite in the presence of a compound which gives H2S by heating. (In an example, 0.5 g. ethylenediamine hydrosulfide is added to a mixture of 13 g. ethylenediamine and 8.9 g. MeCN and the mixture heated to reflux for 5.5 hrs. to give 8.3 g. 2-methylimidazoline.) Similarly prepared are 2,4-dimethylimidazoline, 2-phenylimidazoline, 1,4-bis(2-imidazolinyl)benzene, and 1,4-bis(2-imidazolinyl) butane.

Sawa, N. (Nippon Kagaku Zasshi, 89:780-784, 1968) describes synthesis of 2-substituted 2-imidazolines by the action of elemental sulfur (2,2'-(1,4-phenylene) bis[4,5-dihydro-imidazole). U.S. Pat. No. 2,488,094 describes the preparation of various aromatic diimidazoles, including 2,2'-(1,4-phenylene)bis-benzimidazole.

The synthesis of compounds where both of $R^2$ and $R^3$ are [CH($R^{11}$)CH($R^{12}$) O]$_y$H or ~$R^{10}{}_x$[CH($R^{11}$)CH($R^{12}$)O]$_y$H, such as reflected by Formulas IX and X, can be carried out by adding an oxide to cap the secondary amine groups in the imidazoline rings, such at a temperature in the range of about 80°-140° C. Extension of an alkylene oxide chain from the capped amine groups can be performed using a basic catalyst (e.g., NaOH) at 0.1-1.0 wt. percent based on the final product weight.

Bis-imidazoline compounds of the current disclosure can be present in an aqueous composition used to prevent corrosion of a metal surface that includes copper. The aqueous composition can be one that is premixed with a desired amount of bis-imidazoline corrosion inhibitor, optionally with one or more other components. The premixed composition can then be provided to a system having metal components that includes copper intended to be protected from corrosion.

In other aspects, the aqueous composition is generated by adding the bis-imidazoline compound to water already present in a system. For example, the bis-imidazoline compound can be manually added to an industrial water-containing system. The bis-imidazoline compound can also be metered into an industrial water-containing system using a pump, where the volume of water in the system may be too large to practically premix.

The bis-imidazoline compound-containing compositions can be used to inhibit corrosion in various systems. For example, the compounds can be used as water treatment additives where it is desired to inhibit corrosion of a metal article that includes copper that is in contact with water. Aqueous compositions including the bis-imidazoline corrosion inhibitor, optionally with one or more other components, can be used in exemplary systems such as industrial cooling water systems, automotive cooling water systems, gas scrubbing systems, steam generating systems, evaporation systems, water-based refrigeration systems, milling, boring, cutting, sawing, or machining systems, hydraulic system, and scouring systems.

Components of the system intended to be protected from corrosion using the aqueous compositions can be made entirely or in part from copper and optionally include one or a combination of other metals, such as iron, aluminum, zinc and various alloys of these metals, e.g., steel and other ferrous alloys, such as brass and the like which are generally used in aqueous systems.

The amount of the bis-imidazoline compound added to the aqueous composition can be determined by the specific compound or combination of compounds used, the presence of other reagents in the composition, the operational parameters of the system using the composition, or the type and amount of metal components in the system that are in contact with the composition. For corrosion-inhibition the amount of bis-imidazoline compound in the composition can be in the range of about 0.1 to about 50,000 ppm (i.e., 0.00001 to 5% (wt %)), or more specifically in the range of about 1 to about 500 ppm, or about 1 to about 200 ppm, or about 1 to about 100 ppm.

In addition to the bis-imidazoline compound, the composition can include one or more compounds selected from biocides, polymeric dispersants, scale inhibitors, pH adjusters, surfactants, and anti-foam agents.

To provide corrosion inhibition, the bis-imidazoline compound can be added to water as a single dose, or can be added intermittently (such as in multiple doses) or continuously. The amount of bis-imidazoline compound added to the system can optionally be functionally described as "an effective amount" sufficient to inhibit corrosion of the metal surface that includes copper that the aqueous composition is in contact with. The particular amount of bis-imidazoline compound added can depend on various factors, such as the components the compound is in contact with, operation of the system with the aqueous composition, additional compounds (e.g., biocides, scale inhibitors, dispersants, defoamers) present in the system, etc. Following addition, the concentration of free bis-imidazoline compound in the aqueous composition may decrease as a protective film forms on the metal surfaces that includes copper that are in contact with the aqueous composition.

Additional bis-imidazoline compound can be added to the aqueous composition as needed, such as in an intermittent or continuous manner. In some modes of practice, addition of further bis-imidazoline can be determined knowing performance parameters such as the passivation rate and persistence of the protective layer containing the compounds. The metal surface that includes copper that is in contact with the aqueous composition can also be inspected to determine if the amount of compound added to the composition is sufficient to prevent corrosion of the metal surface of the components. With an understanding of the amount of bis-imidazoline compound sufficient to prevent corrosion in operation, a treatment regiment with intermittent or continuous addition of the compound to the aqueous system can be established.

The aqueous composition containing the bis-imidazoline compound can include a biocide to inhibit growth or organisms in the composition. Various biocides are known in the art as effective for treating bacterial and other eukaryotic microorganisms, such as algae. For example, the biocide can be used to control gram-negative organisms, sessile microbes, sulfate-reducing bacteria, and algal biomass. One, or a combination of biocides, can be present in the composition.

The aqueous composition can include an oxidizing biocide, such as a halogen or halogen-containing oxidizing compound selected from bromine, chlorine, hypochlorous acid, hypochloride salt, chlorine dioxide, iodine, and sodium chlorite. Non-halogen oxidizing compounds include hydrogen peroxide, and potassium permanganate. Oxidizing acids include peracetic acid.

The composition can include a non-oxidizing biocide such as glutaraldehyde; 2-Bromo-4-hydroxyacetophenone (BHAP); dibromonitrilopropionamide (DBNPA; e.g., D-ow™ Antimicrobial 7287); 1,3-dibromo-5,5-dialkylhydantoin (DBDAH); fatty amines (e.g., Mexel™ 432); polyhexamethylene biguanide (PHMB); isothiazolone (e.g., Sea-Nine™; Rohm & Haas); 2-thiocyanomethylthio benzothiazole (TCMTB); sodium dimethyldithiocarbamate (DIBAM); quaternary ammonium compounds such as alkyl-benzyldimethyl ammonium chloride and benzalkonium chloride; chlorothalonil; dichlofluanid; 1-(3-chloroallyl)-3,5,7-triaza-1-azoniaadamantane chloride; 2-methylthio-4-tertbutylarnino-6-cyclo-propylamino-striazine (e.g., Irgarol™1051; Ciba); phenol; sodium hydroxide; triclosan; and thiocarbamate.

Other commercially available biocides include, but are not limited to Nalco™ 7330 (Nalco Energy Services, Sugar Land, Tex.); Biosperse™ XD389 (Ashland), Biocide™ MC 68 WT and Omegaa™ AQ-6171 (Chemetall, New Providence, N.J.).

In some embodiments, the aqueous composition can include both an oxidizing and a nonoxidizing biocide. A composition with two biocide types can benefit from properties of each type of chemical. For example, the oxidizing biocide can, at the outset, kill process contaminants and then afterwards provide a low activity control biostat. The nonoxidizing biocide can be provided periodically for shock treatment to provide microbe killing. The amount of biocide(s) added to the aqueous composition can be chosen based on factors such as the particular biocide, the application in which the aqueous composition is used, the extent of microbial contamination; or the timing of biocide application (e.g., initial or maintenance). The following concentration ranges are for illustrating use of certain biocides for cooling water systems: BHAP at about 1 to 20 mg/L; DIBAM at 40 to 60 mg/L; DBNPA at 25 to 35 mg/L; glutaraldehyde at 100 to 125 mg/L; alkylbenzyldimethyl ammonium chloride or benzalkonium chloride at 50 to 100 mg/L; TCMTB at 20 to 50 mg/L.

The aqueous composition containing the bis-imidazoline compound can include a polymeric dispersant or scale inhibitor. A polymeric dispersant can be effective at dispersing or suspending various solids to prevent them from settling out of solution and forming deposits (scale). Therefore, many polymeric dispersants can also function as scale inhibitors to inhibit the precipitation of calcium salts (e.g., calcium carbonate, calcium sulfate, and calcium phosphate).

If a polymeric dispersant or scale inhibitor is desired for use, it can be chosen based on one or more factors, such as the type and amount of solids in the aqueous composition and the compatibility with other components in the aqueous composition, if present (e.g., biocide), and the operating conditions of the application, including the pH and temperature of the aqueous composition.

Exemplary polymeric dispersants include various polymer types, homopolymers, co-polymer (e.g., block, random), ter-polymer, etc. In some aspects the polymeric dispersant is a water soluble anionically charged polymer. An anionically charged polymer can be formed from polymerization of unsaturated carboxylic acids such as acrylic acid, methacrylic acid, maleic acid or anhydride, itaconic acid or anhydride, allyl acetic acid, and fumaric acid.

The polymer can optionally be formed from an unsaturated sulfonic acid such as 2-acrylamido-2-methylpropyl sulfonic acid (AMPS), 2-methacrylamido-2-methylpropylsulfonic acid, vinyl sulfonic acid, sulfoalkyl acrylate, sulfoalkyl methacrylate, allyl sulfonic acid, 3-methacrylamido-2-hydroxy-propyl sulfonic acid, and sulfonic acid acrylate.

Exemplary polymeric dispersants include poly(acrylic acid) and poly(methacrylic acid) and metal or ammonium salts thereof; acrylic acid-sulfomethylacrylamide acrylamide copolymers (e.g., see U.S. Pat. No. 5,308,498); copolymers of acrylic acid and N,N-dimethylacrylamide or diacetone acrylamide (e.g., see U.S. Pat. No. 4,566,973).

Exemplary polymeric dispersants are also commercially available, e.g., KemGuard™ homopolymer and copolymers (Kemira, Atlanta, Ga.); Optidose™, Acumer™, Tarnol™, Romax™ and polymers (Rohm Haas);

Many commonly used polymeric dispersants have relatively lower polymer molecular weights ("weight average molecular weight" or $M_w$, see, for example, Allcock, H. R. and Lampe, F. W. (1990) *Contemporary Polymer Chemistry*; pg 271). For example, polymeric dispersants having molecular weight of less than about 100,000 Da, or less than about 50,000 Da, such as in the range of about 500 Da to about 50,000 Da, or about 1,000 Da to about 30,000 Da have particular applicability for polymeric dispersants in the aqueous composition.

The amount of polymeric dispersant added to the aqueous composition can be chosen based on factors such as the particular polymer used, the application in which the aqueous composition is used, and compatibility with other composition reagents, if present. Exemplary concentrations range from about 5 to about 50 ppm, or about 10 to about 30 ppm.

The scale inhibitors may also contain non-polymeric scale inhibitors. Exemplary scale inhibitors are phosphonate based compounds, such as are amino phosphonates. Phosphonates act as scale inhibitors by adsorbing onto specific crystal nuclei surfaces of insoluble salts, thereby inhibiting further crystal growth.

Included are aminomethylene phosphonates such as amino-tris(methylenephosphonate) (AMP), 2-hydroxyethyl-amino-bis(methylenephosphonate) (HEABMP), ethylenediamine-tetrakis(methylene-phosphonate) (EDTMP), tetramethylenediamine-tetrakis-(methylenephosphonate) (TDTMP), hexamethylenediamine-tetrakis(methylene-phosphonate) (HDTMP), 2-phosphonobutane-1,2,4-tricarboxylate (PBTC), hydroxyethylydene-1,1-diphosphonate (HEDP), and diethylenetriamine-pentakis(methylenephosphonate) (DETPMP) (e.g., see, Demadis, K. D., and Ketsetzi, A., (2007) Separation Science and Technology, 42: 1639-1649; and U.S. Pat. No. 5,038,861). Phosphate ester, phosphonate, and phosphonic acid scale inhibitors are also commercially available from, for example, Weatherford.

The amount of non-polymeric scale inhibitors added to the aqueous composition can be chosen based on factors such as the inhibitor used, the application in which the aqueous composition is used, and compatibility with other composition reagents, if present. Exemplary concentrations range from about 5 to about 50 ppm, or about 10 to about 30 ppm.

The aqueous composition containing the bis-imidazoline compound can include a surfactant. A surfactant can be useful for removing or breaking up oil deposits on components of cooling water treatment systems. Surfactant classes include nonionic surfactants, anionic surfactants, and cationic surfactants. Surfactant classes; condensates of ethylene oxide with alkyl phenols; polyethyleneoxy ethers of alcohols and mercaptans; difunctional and polyfunctional polyethyleneoxy ethers; and fatty acids of oxidized paraffin wax (see, for example, U.S. Pat. No. 3,578,589) Specific exemplary surfactants include polyethylene glycol 600 dioleate and ethoxylated lauryl alcohol (see WO1996/031749A1).

One exemplary surfactant class is alkoxylated alkyl amine surfactants such as polyoxyalkylene derivatives of fatty acid amines (e.g., polyoxyalkylene tallow amine). Commercially available alkoxylated alkyl amine surfactants include, for example, Ethomeen™ C/15, (Akzo Nobel). Another exemplary surfactant class is quaternary ammonium-based surfactants, such as those that have alkylation, ethoxylation, or propoxylation, or combinations thereof. Exemplary quaternary ammonium surfactants are commercially available under the trademarks Ethoquad™ and Arquad™ (AkzoNobel, Chicago, Ill.). Alkoxylated phosphate esters, such ethoxylated phosphate esters, represent another surfactant class. Commercially available ethoxylated phosphate ester surfactants include Emphos™ (Witco Chemicals, of Brooklyn, N.Y.) and Stepfac™ 8170 (Stepan Co., Northfield, Ill.). Another surfactant class is a disulfonate surfactant, such as alkyl diphenyl ether disulfonates and salts of alkyl diphenyl oxide disulfonates. Exemplary disulfonates include Dowfax 3B2™ (Dow Chemicals, Midland, Mich.) and Fenopon C0436™ (GAF Corp., New York, N.Y.).

Exemplary concentrations of surfactant range from about 1 to about 100000 ppm, or about 10 to about 10000 ppm.

The aqueous composition containing the bis-imidazoline compound can include a pH adjuster. In modes of practice, it can be desirable to control the pH of cooling water treatment systems. For example, a pH adjuster can be used to prevent acidic conditions which otherwise increase the chance of corrosion, and also prevent alkaline conditions which otherwise increase the chance of scale formation.

The option of using a pH adjuster can be made depending on water conditions. Alkaline conditions can be adjusted using acids such as sulfuric acid ($G_2SO_4$) and hydrochloric acid (HCl). The addition of an acid can convert scale forming materials such as calcium carbonate to more soluble forms such as calcium sulfate (e.g., by using sulfuric acid), which in turn prevents scale build up.

In determining the amount of pH adjuster to be added to the aqueous system, one or more indexes can be analyzed, such as the Langlier Saturation Index (LSI) and the Ryznar Saturation Index (RSI). The indexes are utilized for system setup when pH adjustment by acid addition is used for scale control. LSI and RSI indexes provide means of reducing the integrated parameters of calcium, alkalinity, pH, dissolved solids, and temperature to a single value, which indicates the tendency of water to form a calcium scale or promote corrosion. A positive LSI number (RSI less than 5.0) indicates a scale forming water while a negative LSI number (RSI greater than 7.0) indicates a scale dissolving, or corrosive, water. Normal practice is to maintain a slightly positive LSI number, +0.2 to +0.5, (RSI between 5.0 and 6.0) when utilizing pH adjustment by acid addition and add some chemical scale inhibitor to cope with the resultant slight tendency to scale.

If desired, one or more performance aspects of the bis-imidazoline corrosion inhibitor can be measured. For example, performance aspects include passivation and persistency of the corrosion inhibitor on a metal surface that includes copper. Methods and compositions of the disclosure may optionally be described using values obtained from such measurements.

For example, a rate of passivation refers to the amount of time to form a bis-imidazoline-containing film on a metallic surface after the compound has been added to an aqueous composition. The persistency of a bis-imidazolinone-containing film refers to the time the film is present on a metallic surface when the corrosion inhibitor is not present (e.g. added to) in an aqueous system.

Example 1

Reference Example

Preparation of Phenyl and Tolyl Imidazoline

Synthesis of 2-Phenyl Imidazoline 17 g (0.28 mol) of ethylenediamine (EDA) was taken in a 100 ml RBF (round bottom flask). 20 g (0.14 mol) of benzoyl chloride was gradually added to EDA with constant stirring at 0° C. The reaction mixture was refluxed at 120° C. for 2 h. Temperature was enhanced progressively up to 200° C. and kept for heating there for 2 h. Water was removed at 300° C., under vacuum. Compound was analyzed by using NMR and LCMS techniques.

Spectral data for 2-phenyl imidazoline: $^1$H NMR (400 MHz, $D_2O$) δ: 3.79 (4H, m, —$CH_2$); 7.43 (1H, t, —NH); 7.52-7.83 (5H, m, Aromatic —H); $^{13}$C NMR (400 MHz, $D_2O$) δ: 44.5, 127.9, 128.7, 129.3, 134.6, 166.5; MS (EI) m/z: 147.09 (100%).

Synthesis of 2-(p-Tolyl) Imidazoline 10 g (0.0646 mol) of p-toluoyl chloride was added slowly into 7.76 g (0.13 mol) of FDA with constant stirring at 0° C. in a 100 ml RBF. The reaction mass was refluxed at 100-120° C. for 3 h. Reaction temperature was increased up to 200° and it was maintained there for 2 h. Then, reaction mass was heated at 280-300° C. under reduced pressure to remove water and excess of EDA. The product obtained was analyzed by using NMR and LCMS techniques. The reaction scheme for the synthesis of 2-phenyl and 2-(p-tolyl) imidazoline is shown as follows. Spectral data for 2-(p-tolyl) imidazoline: $^1$H NMR (400 MHz, $D_2O$) δ: 2.34 (3H, t); 3.76 (4H, t, 2×—$CH_2$); 7.43 (1H, t, —NH); 7.28-7.71 (4H, m, Aromatic —H); $^{13}$C NMR (400 MHz, $D_2O$) δ: 20.8, 44.3, 119, 127.8, 129.9, 146.3, 166.3; MS (EI) m/z: 161.1 (100%).

Where, R = phenyl-, p-tolyl-

Example 2

Preparation of Phenyl Bis-Imidazoline

Synthesis of bis imidazoline derivative i. e. 1, 4-bis (4, 5-dihydro-1H-imidazol-2-yl) benzene 10 g (0.05 mol) of terephthaloyl chloride was taken into 100 ml RBF. 11.8 g (0.19 mol) of EDA was gradually added to terephthaloyl chloride at 0° C. with constant agitation at 500 RPM. The reaction mass was stirred at R. T. (room temperature) for 1 h and then, heated at 100-120° C. for 3 h.

Reaction temperature was increased continuously up to 280-300° C. and heated the mixture for 2 h. Water was removed simultaneously by using vacuum distillation assembly.

The product was analyzed by NMR and LCMS methods. Spectral data for 1, 4-bis (4, 5-dihydro-1H-imidazol-2-yl) benzene: $^1$H NMR (400 MHz, $D_2O$) δ: 3.79 (8H, m, 4×—$CH_2$); 7.43 (2H, t, —NH); 8.1 (4H, m, Aromatic —H); $^{13}$C NMR (400 MHz, $D_2O$) δ: 48.8, 129.3, 136.3, 165.74; MS (EI) m/z: 215.12 (100%).

Example 3

Corrosion Testing

Corrosion inhibition performance evaluation trials were conducted using a metal coupon testing protocol largely based on the guidelines of the ASTM G31-72 standard. Copper coupons fabricated as per IS 1972 and sized 50 mm×25 mm×2 mm were used as test pieces for the experiments. Dilute nitric acid (3.5% w/w) was used as the test solution and was maintained at a temperature of 50° C. under agitation at a speed of 300 rpm during the test period. This represents a significantly oxidizing type of system with accelerated testing conditions compared to the typical field conditions encountered in industrial copper corrosion inhibition. In the blank run, the metal coupon was cleaned/dried and weighed before the trial, kept immersed in the dilute acid solution under the process conditions for 4 hours during the test, then removed from the solution, cleaned/dried and weighed again. The mass loss of the coupon (~1.3%) was used as a measure of the extent of corrosion in the test piece under the test conditions. In the performance evaluation run, the additive (inhibitor) sample was added to the test solution at a specific dosage and stirred for adequate dispersion, before introducing the metal coupon in the system. The procedure for determining the mass loss in the coupon as well as the test conditions were same as those used for the blank run. The corrosion inhibition performance of the additive was calculated as follows:

$$\% \text{ corrosion inhibition} = \left[1 - \frac{\text{mass loss with additive}}{\text{mass loss without additive}}\right] \times 100$$

The performance evaluation results obtained showed the bis-imidazoline compound provided better corrosion inhibition over non-bis compounds for metals such as copper even in stringent test conditions. The bis-imidazoline compound demonstrated similar performance as the benchmark standards (triazoles). Non-aromatic bis-imidazolines and/or non-imidazoline compounds (aliphatic fatty acid based, aminoethylpiperazine derived aromatic amides) show a deterioration in inhibition performance suggesting the requirement for both aromaticity and a bis-imidazoline moiety in the molecule to obtain effective copper corrosion inhibition under stringent conditions.

TABLE 1

| S.N. | Additive | Structure | Dosage (ppm) | % Corrosion inhibition |
|---|---|---|---|---|
| 1 | Blank (no inhibitor) | — | — | 0.0 |
| 2 | Tolyltriazole | | 100 | 99.0 |
| 3 | Benzotriazole | | 100 | 99.1 |
| 4 | Phenyl imidazoline | | 100 | 96.6 |

TABLE 1-continued

| S.N. | Additive | Structure | Dosage (ppm) | % Corrosion inhibition |
|---|---|---|---|---|
| 5 | Tolyl imidazoline |  | 100 | 96.1 |
| 6 | Phenyl bis-imidazoline |  | 100 | 98.5 |
| 7 | Oleic acid + EDA bis-imidazoline |  | 100 | 23.7 |
| 8 | Dipicolinic acid-AEP based diamide |  | 100 | 54.3 |

Example 4

Thermal Stability

Figure 1:
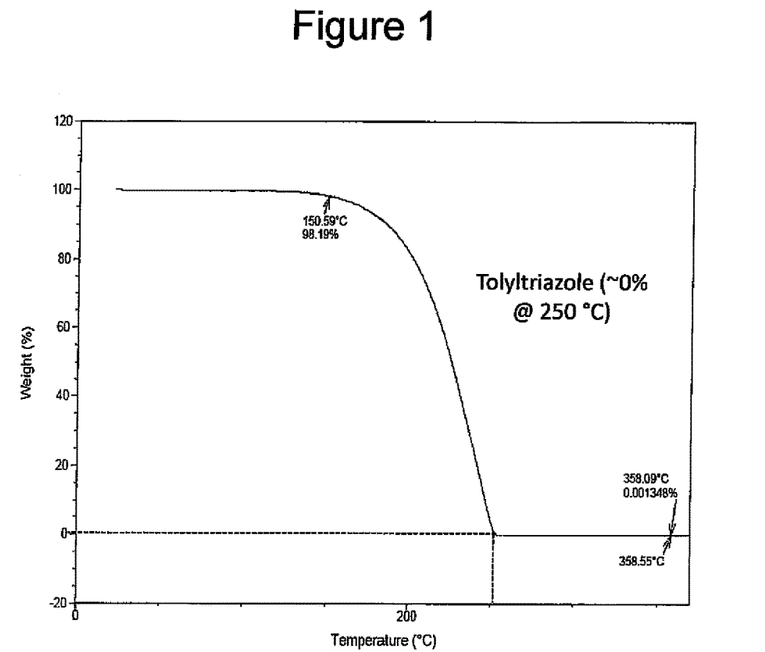
FIG. 1 is a graph showing results from thermo-gravimetric analysis of tolyltriazole.
Figure 2:
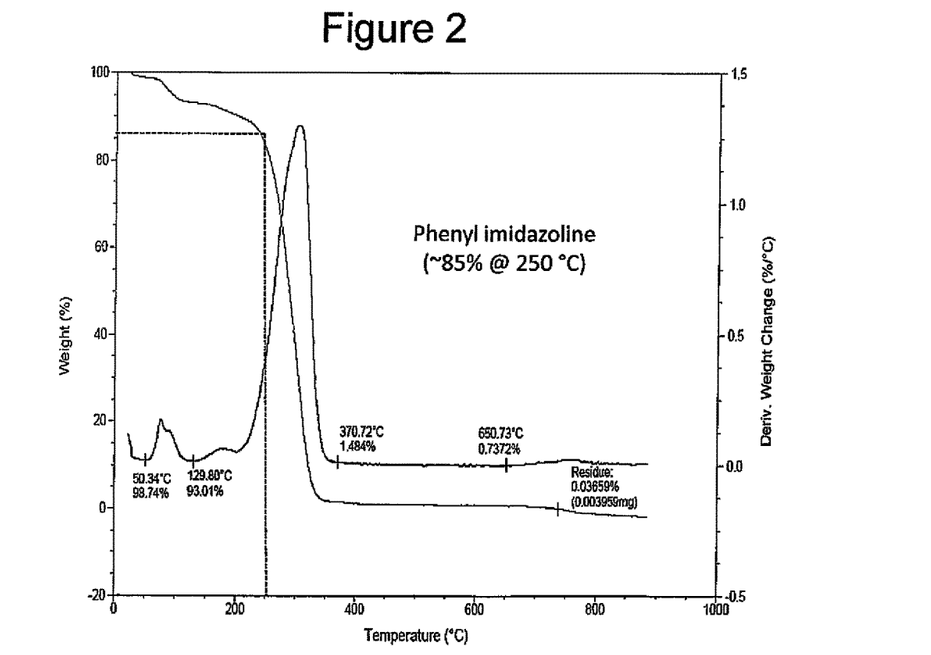
FIG. 2 is a graph showing results from thermo-gravimetric analysis of phenyl imidazoline.
Figure 3:
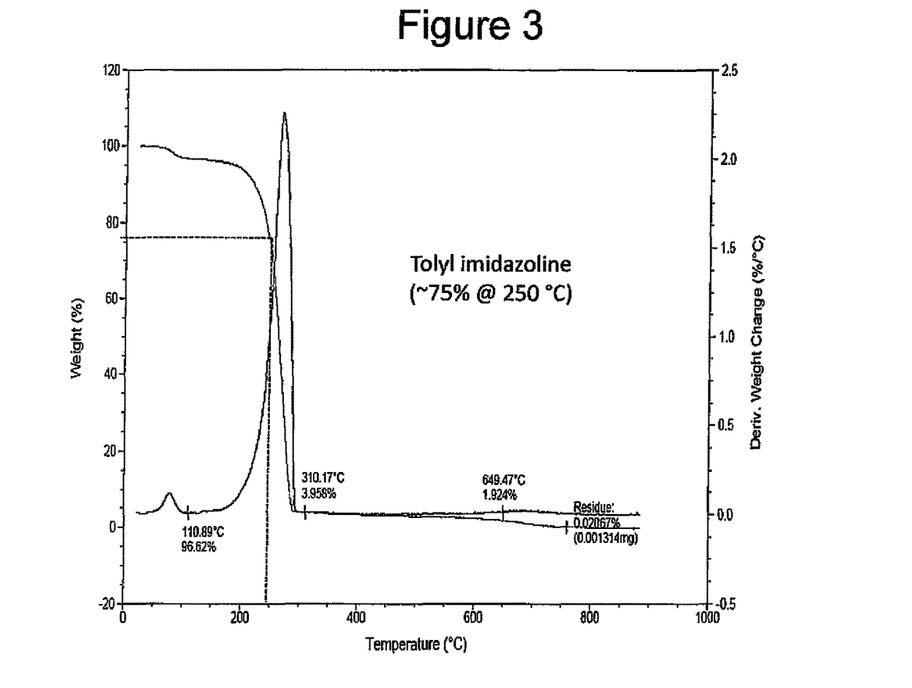
FIG. 3 is a graph showing results from thermo-gravimetric analysis of tolyl imidazoline.
Figure 4:
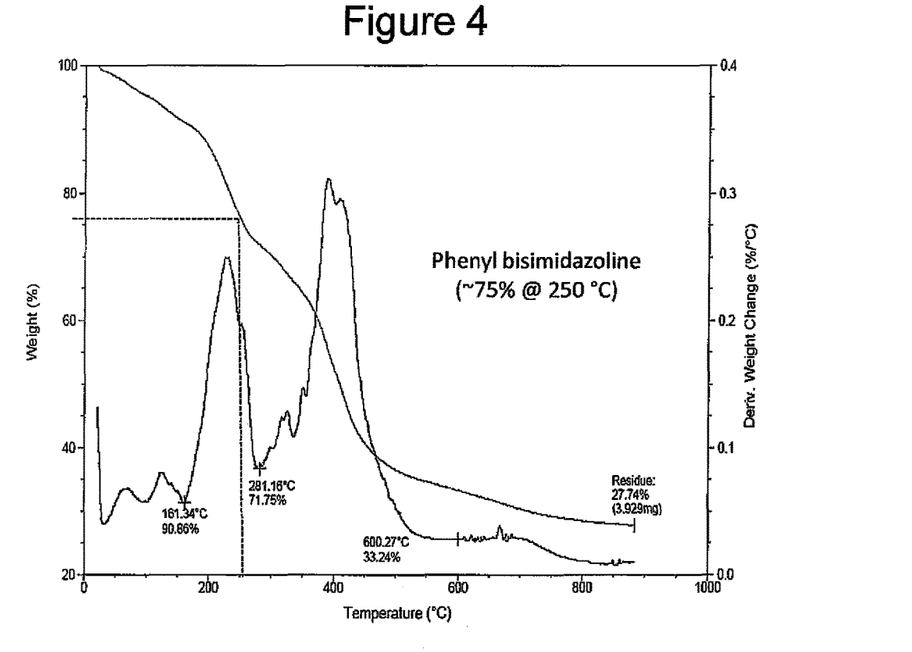
FIG. 4 is a graph showing results from thermo-gravimetric analysis of phenyl bis-imidazoline.

Thermal stability testing was performed on compositions including tolyltriazole, phenyl imidazoline, tolyl imidazoline, and phenyl bis-imidazoline using thermo-gravimetric analysis.

The thermo-gravimetric analysis of the samples was carried out using TA instrument Q 500 model with EVA furnace. About 5 to 15 mg sample was taken in a clean platinum sample pan. The analysis was performed at a heating rate of 10° C. per minute from ambient temperature to 900° C. in a nitrogen atmosphere. The flow rate of sample purge gas and balance were 90 ml/min and 10 ml/min respectively.

What is claimed is:

1. A method of inhibiting corrosion of an article comprising a metal surface that includes copper in an aqueous system, the method comprising a step of contacting the article with an aqueous composition comprising a compound of Formula I:

wherein $R^1$ is a partially or fully unsaturated, single or fused cyclic C3-C14 hydrocarbylene group having aromaticity, optionally substituted and optionally having one or more heteroatoms; and wherein $R^2$, $R^3$, $R^4$, $R^5$, $R^6$, and $R^7$ are independently selected from H and $R^8$, wherein $R^8$ is a linear or branched hydrocarbyl group optionally including one or more N, O, or S heteroatoms.

2. The method of claim 1 wherein $R^1$ is an arylene group, optionally ring substituted.

3. The method of claim 2 wherein $R^1$ is selected from phenylene, naphthylene, anthracylene, phenanthrylene, biphenylene and indylene, optionally ring substituted.

4. The method of claim 3 wherein $R^1$ is phenylene, optionally ring substituted.

5. The method of claim 1 wherein the compound is of Formula V:

wherein, $R^{10}$ is ~(CH$_2$CH$_2$NH)~, and x is 0 or an integer in the range of 1-3.

6. The method of claim 5 wherein the compound has the formula:

7. The method of claim 1, wherein the compound is of Formula IV:

wherein $R^9$ is H, a halogen, or a linear, branched or cyclic hydrocarbyl group, optionally including one or more heteroatoms, and wherein n is 0, or an integer in the range of 1-4, and wherein $R^2$-$R^7$ are as defined herein.

8. The method of claim 1, wherein the compound is:

9. The method of claim 1 wherein the compound is of Formulas IX and X, respectively, as follows:

-continued wherein $R^{10}$ is ~($CH_2CH_2NH$)~, x is 0 or an integer in the range of 1-3, $R^{11}$ and $R^{12}$ are independently selected from the group consisting of hydrogen methyl and/or ethyl; y is 0 (a covalent bond) or an integer in the range of 1-5.

10. The method of claim 1 wherein the composition comprises one or more component(s) selected from the group consisting of a dispersant, a surfactant, a pH adjuster, a biocide, a scale inhibitor, and a defoamer.

11. The method of claim 1 wherein the aqueous composition is used as a heat exchange agent in an industrial application.

12. An aqueous composition capable of inhibiting corrosion of an article comprising a metal surface that includes copper, the composition comprising
  (a) a corrosion inhibiting amount of a compound of Formula I of claim 1; and
  (b) one or more component(s) selected from the group consisting of a dispersant, a surfactant, a pH adjuster, a biocide, a scale inhibitor, and a defoamer.

13. A method for preparing an aryl bis-imidazoline compound comprising a step of reacting an aryl acid or aryl acid halide with an alkylene diamine to provide an aryl bis-imidazoline compound, wherein during reacting the temperature is increased.

14. The method of claim 13 wherein the aryl acid or aryl acid halide is a compound of Formula XI:

wherein $R^{13}$ is a halogen, or a linear, branched or cyclic hydrocarbyl group, optionally including one or more heteroatoms, wherein X is a halogen or ~OH, and wherein n is 0, or an integer in the range of 1-4, and y is 2, and the alkylene diamine is a compound of Formula XII, wherein $R^{14}$ and $R^{15}$ are independently selected from H and hydrocarbyl groups optionally including one or more N, O, or S heteroatoms, and m=2.

15. The method of claim 13 wherein the aryl halide is terephthaloyl chloride and the alkylene diamine is ethylene diamine.

16. The method of claim 13 wherein reacting includes reacting at temperatures in the range of about 100° C. to about 325° C.

17. A method of inhibiting corrosion of an article comprising a metal surface that includes copper in an aqueous system, the method comprising a step of contacting the article with an aqueous composition comprising a compound selected from the group consisting of
a compound of Formula V:

wherein, $R^{10}$ is ~($CH_2CH_2NH$)~, and x is 0 or an integer in the range of 1-3;
a compound of Formula IX or Formula X:

Formula IX

Formula X wherein $R^{10}$ is ~($CH_2CH_2NH$)~, x is 0 or an integer in the range of 1-3, $R^{11}$ and $R^{12}$ are independently selected from the group consisting of hydrogen methyl and/or ethyl; y is 0 (a covalent bond) or an integer in the range of 1-5; and 18. The method of claim 17 wherein the composition comprises one or more component(s) selected from the group consisting of a dispersant, a surfactant, a pH adjuster, a biocide, a scale inhibitor, and a defoamer.

19. The method of claim 17 wherein the aqueous composition is used as a heat exchange agent in an industrial application.

* * * * *